(12) United States Patent
Worley et al.

(10) Patent No.: US 7,335,373 B2
(45) Date of Patent: Feb. 26, 2008

(54) BIOCIDAL SILOXANE COATING MATERIAL CONTAINING N-HALOGENATED AMINE AND AMIDE FUNCTIONAL GROUPS

(75) Inventors: Shelby D. Worley, Auburn, AL (US); Yongjun Chen, Bellevue, WA (US); Jie Liang, Auburn, AL (US); Rong Wu, Auburn, AL (US); Kevin Barnes, Opelika, AL (US); Royall M. Broughton, Valley, AL (US); Unchin Cho, Auburn, AL (US); Jaewoong Lee, Auburn, AL (US)

(73) Assignee: Auburn University, Auburn, AL (US)

( * ) Notice: Subject to any disclaimer, the term of this patent is extended or adjusted under 35 U.S.C. 154(b) by 561 days.

(21) Appl. No.: 10/991,358

(22) Filed: Nov. 17, 2004

(65) Prior Publication Data
US 2005/0186173 A1  Aug. 25, 2005

Related U.S. Application Data

(60) Provisional application No. 60/520,608, filed on Nov. 17, 2003.

(51) Int. Cl.
*A01N 43/40* (2006.01)
*C07D 471/10* (2006.01)

(52) U.S. Cl. ............... 424/405; 546/14; 546/20; 424/78.32; 424/78.36; 428/446; 526/262; 526/265; 528/27

(58) Field of Classification Search ............ 424/405, 424/78.32, 78.36; 546/14, 20; 428/446; 526/262, 265; 528/27
See application file for complete search history.

(56) References Cited

U.S. PATENT DOCUMENTS

| | | | |
|---|---|---|---|
| 3,560,385 A | 2/1971 | Roth | |
| 3,730,701 A | 5/1973 | Isquith et al. | |
| 3,794,736 A | 2/1974 | Abbott et al. | |
| 3,814,739 A | 6/1974 | Takeda | |
| 3,846,442 A | 11/1974 | Habermeier et al. | 260/309.5 |
| 3,860,709 A | 1/1975 | Abbott et al. | |
| 3,979,477 A | 9/1976 | Schmid et al. | 260/835 |
| 4,206,104 A | 6/1980 | Dowbenko et al. | 260/29.3 |
| 4,282,366 A | 8/1981 | Eudy | |
| 4,322,522 A | 3/1982 | Johnson et al. | |
| 4,408,996 A | 10/1983 | Baldwin | |
| 4,412,078 A | 10/1983 | Berger | |
| 4,414,268 A | 11/1983 | Baldwin | |
| 4,504,541 A | 3/1985 | Yasuda et al. | |
| 4,615,937 A | 10/1986 | Bouchette | |
| 4,692,374 A | 9/1987 | Bouchette | |
| 5,194,504 A | 3/1993 | Lebovits et al. | |
| 5,463,058 A * | 10/1995 | Carrozza et al. | 546/14 |
| 5,490,983 A | 2/1996 | Worley et al. | |
| 5,882,357 A | 3/1999 | Sun et al. | |
| 5,902,818 A | 5/1999 | Worley et al. | |
| 5,954,869 A | 9/1999 | Elfersy et al. | |
| 6,770,287 B1 | 8/2004 | Sun et al. | 424/404 |
| 2003/0056297 A1 | 3/2003 | Sun | 8/115.51 |
| 2004/0127667 A1 | 7/2004 | Worley et al. | |

FOREIGN PATENT DOCUMENTS

DE    2 227 689    12/1972

(Continued)

OTHER PUBLICATIONS

Lin, Jian, Winkelman, Catherine, Worley, S.D., Broughton, R.M., Williams, J.F., "Antimicrobial Treatment of Nylon," J. Appl. Polym. Sci., 81:943-947 (2001).

(Continued)

*Primary Examiner*—Charanjit S. Aulakh
(74) *Attorney, Agent, or Firm*—Haverstock & Owens, LLP

(57) ABSTRACT

N-halamine compounds which contain hindered amine and amide functional groups. Compounds include

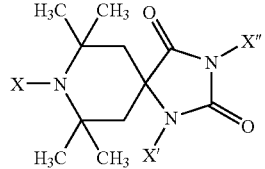

wherein X, X', and X" independently are H, Cl, or Br, wherein no more than two of X, X', and X" are H and

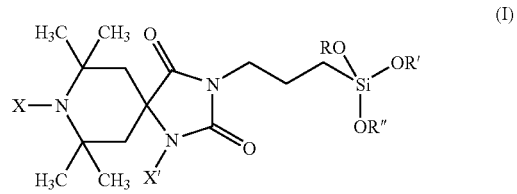

(I)

wherein R, R', and R" are independently alkyl groups containing 1 to 4 carbon atoms or hydrogen, and X and X' are independently H, Cl, or Br. Compositions comprising the compounds are also described. The compounds and/or compositions can be used, for example, for the purpose of constructing biocidal coatings and materials. The biocidal activity can inactivate pathogenic microorganisms such as bacteria, fungi, and yeasts, as well as, virus particles.

34 Claims, No Drawings

FOREIGN PATENT DOCUMENTS

| | | |
|---|---|---|
| DE | 26 23 464 A1 | 12/1976 |
| DE | 44 07 947 C2 | 9/1994 |
| EP | 0 101 720 B1 | 12/1987 |
| JP | 49 061238 | 6/1974 |
| WO | WO 83/02909 | 9/1983 |

OTHER PUBLICATIONS

Lin Jian, Winkelmann, Catherine, Worley, S.D., Kim, Jangho, Wei, C-I., Cho, Unchin, Broughton, R.M., Santiago, J.I., Williams, J.F., "Biocidal Polyester," J. Appl. Polym. Sci., 85:177-182 (2002).

Nurdin, N., Helary, G., Sauvet, G., "Biocidal Polymers Active by Contact. II. Biological Evaluation of Polyurethane Coatings with Pendant Quaternary Ammonium Salts," J. Appl. Polym. Sci., 50:663-670 (1993).

Nurdin, N., Helary, G., Sauvet, G., "Biocidal Polymers Active by Contact. III. Ageing of Biocidal Polyurethane Coatings in Water," J. Appl. Polym. Sci. 50:671-678 (1993).

Panangala, V.S., Liu, Li, Sun, G., Worley, S.D., Mitra, A., "Inactivation of rotavirus by new polymeric water disinfectants," J. Virolog. Meth. 66:263-268 (1997).

Sun, Gang, Wheatley, Walter B., Worley, S.Davis,"A New Cyclic N-Halamine Biocidal Polymer," Ind. Eng. Chem. Res. 33:168-170 (1994).

Sun, Gang, Allen, Leslie C., Luckie, E. Paige, Wheatley, Walter B., Worley, S. Davis,"Disinfection of Water by N-Halamine Biocidal Polymers," Ind. Eng. Chem. Res. 34(11), 4106-4109 (1995).

Sun, G., Chen, T.Y., Habercom, M.S., Wheatley, W.B., Worley, S.D.,"Performance Of A New Polymeric Water Disinfectant," Water Res. Bull. 32(4), 793-797 (1996).

Worley, S.D. Ph,D., Williams, J.F. Ph.D.,"Disinfection of Water by N-Halamine Biocidal Polymers," Water Cond. & Pur. 39:96-100 (1997).

Worley, S.D., Sun, G.,"Biocidal Polymers," Trends in Polym. Sci. 4(11), 364-370 (1996).

* cited by examiner

BIOCIDAL SILOXANE COATING MATERIAL CONTAINING N-HALOGENATED AMINE AND AMIDE FUNCTIONAL GROUPS

CROSS REFERENCE TO RELATED APPLICATIONS

This application claims priority to U.S. Provisional Application Ser. No. 60/520,608, filed Nov. 17, 2003, hereby incorporated by reference in its entirety for all of its teachings.

ACKNOWLEDGEMENTS

This invention was made with government support under Grant F08637-02-C-7020 awarded by the United States Air Force. The government may have certain rights in the invention.

BACKGROUND

Previous attempts to incorporate biocidal activity into materials and coatings have primarily involved two methods—1) physical mixing (blending) of biocides into the materials and coatings and 2) chemical binding of biocidal functional groups to the polymers or copolymers making up the materials and coatings. Chemical binding should be preferable for long-term biocidal activity if the bound biocidal functionality does not adversely affect the other desired properties of the material or coating, such as strength, appearance, and chemical resistance.

For example, a significant amount of work has been performed concerning rendering sponges biocidally active. This involves encapsulation of a variety of weak biocides into the porous structure of the sponge, either through physical blending or chemical bonding to the surface. The sponges modified in this manner can exhibit biocidal activity, but the contact times necessary for action are generally long, and some pathogens are not inactivated even at contact times of several hours.

Anti-fouling polyurethanes have been prepared by chemical incorporation of tributyl tin (as described, e.g., in U.S. Pat. No. 5,194,504) and quaternary ammonium salts (see, for example, *J. Appl. Polym. Sci.* 50: 663 (1993); *J. Appl. Polym. Sci.* 50: 671 (1993)). Coatings containing organo-tin compounds are being discredited as threats to the environment, and poly-quats are weak biocides which are nonregenerable. Thus, there is a definite need for more effective biocidal coatings and materials.

A new class of biocidal monomers and polymers known as N-halamines, which could be useful in producing biocidal coatings, has recently been developed. A non-toxic, non-irritating, and cost effective material named poly-1,3-dichloro-5-methyl-5-(4'-vinylphenyl)hydantoin, which is an inexpensive derivative of polystyrene, was first described in U.S. Pat. No. 5,490,983. Subsequent disclosures of its biocidal properties for use in disinfecting applications for water filters have recently occurred [see *Ind. Eng. Chem. Res.* 33:168 (1994); *Water Res. Bull.* 32:793 (1996); *Ind. Eng. Chem. Res.* 34:4106 (1995); *J. Virolog. Meth.* 66:263 (1997); *Trends in Polym. Sci.* 4:364 (1996); *Water Cond. & Pur.* 39:96 (1997)]. The polymer is effective against a broad spectrum of pathogens including *Staphylococcus aureus, Pseudomonas aeruginosa, Escherichia coli, Candida albicans, Klebsiella terrigena*, poliovirus, and rotavirus, among others, causing large log reductions of pathogens with contact times on the order of a few seconds in water disinfection applications. N-halamine functional groups such as hydantoins, oxazolidinones, and imidazolidinones have also been employed recently in producing biocidal cellulose (U.S. Pat. No. 5,882,357), biocidal films on surfaces (U.S. Pat. No. 5,902,818), biocidal nylon (Lin, et al., *J. Appl. Polym. Sci.*, 81,943 (2001)), and biocidal polyester (Lin, et al., *J. Appl. Polym. Sci.*, 85, 177 (2002)); these patents and articles are hereby incorporated by reference for all of their teachings.

Almost two decades ago, Berger taught in U.S. Pat. No. 4,412,078 the composition and use of a series of alkyl and alkoxy silylpropylhydantoin derivatives as coupling agents for bonding glass fibers to organic resins and as self-bonding adhesion promoters for room-temperature curable silicone adhesives. Berger did not contemplate or teach the halogenation of such derivatives before or after bonding to a surface to render the surface biocidal.

Much work has been done concerning attaching quaternary ammonium functional groups, which are weak, nonregenerable biocides, to various silicon compounds which can then be bonded to surfaces to render them weakly biocidal, e.g., see, U.S. Pat. Nos. 3,560,385; 3,730,701; 3,794,736; 3,814,739; 3,860,709; 4,282,366; 4,504,541; 4,615,937; 4,692,374; 4,408,996; 4,414,268; and 5,954,869.

U.S. application Ser. No. 10/400,165 (publication U.S. 2004/0127667 A1) discloses the use of siloxane monomers and polymers containing N-halamine functional groups having an advantage over previous technology in biocidal efficacy in terms of both the required contact times and increased spectrum of activity against pathogens.

Work has been done previously on unhalogenated TTDD (7,7,9,9-tetramethyl-1,3,8-triazaspiro[4.5]decane-2,4-dione) and its derivatives (the monomeric starting material for the precursor N-halaminesiloxane monomers and polymers taught herein) for use in light and heat stabilization of polymers such as polypropylene (for example, see DE 76-2623464, DE 94-4407947, CAN 116:153052, EP 78-101720, JP 49061238, DE 72-2227689, FR 19670908, U.S. Pat. No. 4,322,522); however, none of these references contemplates or teaches the halogenation of this material or its derivatives before or after infusion into or bonding to a surface to render the surface biocidal.

SUMMARY OF THE INVENTION

The invention includes various biocidal compounds and compositions. These compounds and compositions can be coated on, attached to, or incorporated in a material to control and/or eliminate microorganisms. Also included are methods of making and using the compounds and compositions.

In one aspect, the present invention relates to a N-halamine compound containing amide, imide, and hindered amine functional groups in which none of the nitrogen moieties have hydrogen atoms bonded to the carbon atoms alpha to them. The compound can be provided, for example, as a monomer or a polymer. The present invention also relates to a composition of the N-halamine compound. A molecule having this combination of functionalities (or a composition comprising this molecule) can be, for example, coated onto or infused into a surface or blended with a surface material during production. The compound or composition so introduced on or in a surface can be halogenated with chlorine or bromine to produce a material with biocidal properties.

One example of such a compound is shown below in structure TTDD

TTDD

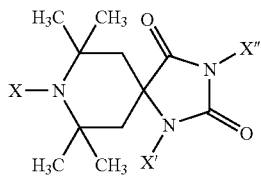

wherein X, X', and X" are, independently, H, Cl, or Br. A biocidal TTDD has no more than two of X, X', and X" being H.

In a second aspect, the present invention relates to a compound of the precursor N-halaminesiloxane or a halogenated N-halaminesiloxane compound depicted in structure I below,

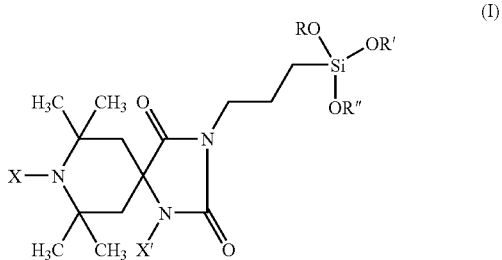

wherein R, R', and R" are, independently, an alkyl group containing 1 to 4 carbon atoms or hydrogen, and wherein X and X' are, independently, a hydrogen atom when the monomer is not biocidal and wherein at least one of X and X' are, independently, a chlorine or bromine atom when the monomer is biocidal. The invention also relates to a composition comprising this compound. This compound can serve, for example, as a monomer for creating a polymer or co-polymer.

A third aspect of the present invention relates to a N-halaminesiloxane polymer or copolymer comprising the monomer depicted in structure I, polymerization occurring through the siloxane oxygen atoms with at least one oxygen atom bonded to hydrogen, and wherein X and X' independently are a hydrogen atom when the monomer is not biocidal or wherein at least one of X and X' independently are a chlorine or bromine atom when the monomer biocidal. The N-halaminesiloxane can be unhalogenated or halogenated.

A fourth aspect of the present invention relates to a surface or material which a precursor N-halaminesiloxane monomer, polymer, or copolymer or halogenated N-halaminesiloxane monomer, polymer, or copolymer has been attached to physically or chemically or has been blended with.

A fifth aspect of the present invention relates to a method of rendering a surface or material biocidal by attaching (physically or chemically), through the hydroxyl moieties, or blending with a monomer, polymer, or copolymer defined above, wherein at least one of X, X', and X" is Cl or Br.

A sixth aspect of the present invention relates to a method of rendering a surface or material biocidal by attaching (physically or chemically), through the hydroxyl moieties, or blending with a monomer, polymer, or copolymer defined above, wherein X and X' are H, and then exposing the thus modified surface or material to a source of oxidative chlorine or bromine.

The present invention relates to the synthesis and use of a precursor or N-halamine monomer and/or polymer which contains both amine and amide functional groups. The compositions can be used, for example, for the purpose of constructing coatings and materials which can be rendered biocidal. The coating or material can be rendered biocidal by exposure to halogen solutions either before or after curing the coating or material. The biocidal coatings and materials can be used to inactivate pathogenic microorganisms, such as bacteria, fungi, and yeasts, as well as virus particles, which can cause infectious diseases, and those microorganisms which cause noxious odors and unpleasant coloring, such as mildew. The coatings are compatible with a wide variety of substrates including, for example, cellulose, chitin, chitosan, synthetic fibers, glass, ceramics, plastics, rubber, cement grout, latex caulk, porcelain, acrylic films, vinyl, polyurethanes, silicon tubing, marble, metals, metal oxides, and silica.

Additional advantages will be set forth in part in the description which follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

DETAILED DESCRIPTION

Before the present compounds, compositions, articles, devices, and/or methods are disclosed and described, it is to be understood that the aspects described below are not limited to specific synthetic methods; specific synthetic methods may, of course, vary. It is also to be understood that the terminology used herein is for the purpose of describing particular aspects only and is not intended to be limiting.

In this specification and in the claims which follow, reference will be made to a number of terms which shall be defined to have the following meanings:

It must be noted that, as used in the specification and the appended claims, the singular forms "a," "an," and "the" include plural referents unless the context clearly dictates otherwise. Thus, for example, reference to "an unhalogenated compound" can include two or more such compounds, reference to "a monomer" includes mixtures of two or more such monomers, and the like.

"Optional" or "optionally" means that the subsequently described event or circumstance can or cannot occur, and that the description includes instances where the event or circumstance occurs and instances where it does not.

Ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

References in the specification and concluding claims to parts by weight, of a particular element or component in a composition or article, denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent of a component, unless specifically stated to the contrary, is based on the total weight of the formulation or composition in which the component is included.

Variables such as X, X', X", R, R', or R" used throughout the application are the same variables as previously defined unless stated to the contrary.

The term "alkyl group" as used herein is a branched or unbranched saturated hydrocarbon group of 1 to 4 carbon atoms, such as methyl, ethyl, n-propyl, isopropyl, n-butyl, isobutyl, t-butyl, and the like.

As used herein, the term "activity" means biocidal activity.

As used herein, the term "biocidal" means activity which inactivates or kills microorganisms.

As used herein, "unhalogenated TTDD" refers to the structure of 7,7,9,9-tetra methyl-1,3,8-triazaspiro[4.5]decane-2,4-dione below:

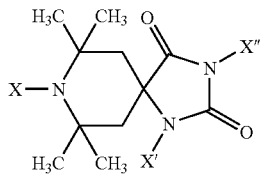

TTDD wherein X, X', and X" are all H.

As used herein, "halogenated TTDD" refers to the structure of 7,7,9,9-tetramethyl-1,3,8-triazaspiro[4.5]decane-2,4-dione below:

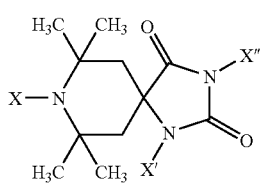

TTDD wherein X, X', and X" are independently H, Cl, or Br, but no more than two of these are H.

As used herein, "precursor" means any compound to which additional oxidative halogens can be added by reaction.

As used herein, "unhalogenated precursor monomer" refers to the structure I below:

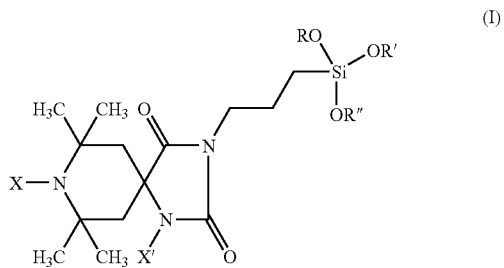

(I)

wherein R, R', and R" independently are alkyl groups containing 1 to 4 carbon atoms or hydrogen, and X and X' are a hydrogen atom.

As used herein, "unhalogenated precursor polymer" refers to a polymer or copolymer comprising a monomer of structure I formed through the siloxane oxygen atoms, but with at least one oxygen atom bonded to hydrogen, and X and X' are each hydrogen.

As used herein, "halogenated precursor monomer" refers to the structure I below:

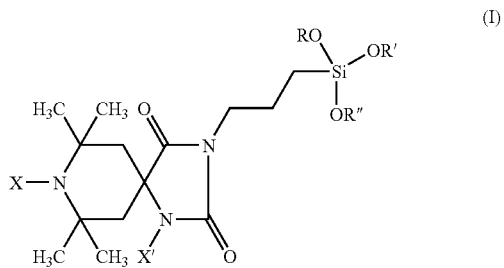

(I)

wherein R, R', and R" independently are an alkyl group containing 1 to 4 carbon atoms or hydrogen, and wherein at least one of X and X' are a chlorine or bromine atom.

As used herein, "halogenated precursor polymer" refers to a polymer or copolymer comprising a monomer of structure I formed through the siloxane oxygen atoms, but with at least one oxygen atom bonded to hydrogen, and wherein at least one of X or X' is chlorine or bromine.

As used herein, "functionalized surface or material" refers to a surface or material to which a species having structure I or structure TTDD, or a polymer or copolymer thereof, as described above, has been attached (physically or chemically) through the hydroxyl moieties or has been blended. If at least one of X or X' in the N-halamine functional group is Cl or Br, the surface or material will be biocidal; if X and X' in the functional group are H, the surface or material will not be biocidal, but the surface or material can be rendered biocidal by exposing it to a source of oxidative chlorine or bromine.

The present invention may be understood more readily by reference to the following detailed description of specific embodiments and the examples included therein.

A. Compounds/Compositions

In one aspect described herein are N-halamine compounds containing amide, imide, and hindered amine functional groups in which none of the nitrogen moieties have hydrogen atoms bonded to the carbon atoms alpha to them.

In one aspect described herein are compounds having the formula TTDD.

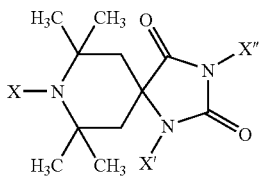

wherein X, X', and X" are independently H, Cl or Br, with no more than two of X, X', and X" being H.

Unhalogenated TTDD is known (for example, see DE 76-2623464, DE94-4407947, CAN 116:153052, EP78-101720, JP49061238, DE 72-2227689, FR 19670908, U.S. Pat. No. 4,322,522); however, none of these references contemplates or teaches the halogenation of this material or its derivatives before or after infusion into or bonding to a surface to render the surface biocidal. These references are hereby incorporated by reference for their teachings on how to make unhalogenated TTDD and its derivatives. Unhalogenated TTDD (and its derivatives) can be used as a starting material for the compound in formula I.

Halogenated TTDD can be used as a biocidal material, for example, as described below. It can be made from unhalogenated TTDD. Halogenated TTDD can be used as a starting material for the formula I compounds.

In another aspect described herein are compounds having the formula I.

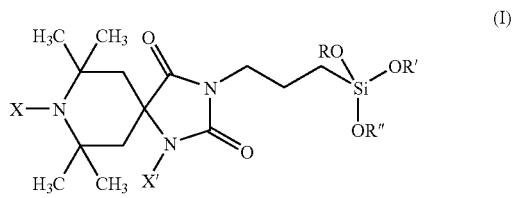

wherein R, R', and R" independently are alkyl groups containing 1 to 4 carbon atoms or hydrogen, and wherein X and X' independently are a hydrogen, chlorine or bromine atom.

An unhalogenated compound of formula I can be synthesized by a method described below.

A halogenated compound of formula I can be synthesized by a method described below.

It is believed that coatings containing the N-halamine siloxanes derived from 7,7,9,9-tetramethyl-1,3,8-triazaspiro [4.5]decane-2,4-dione (described below) will contain halogen stabilized from light accentuated losses due to the presence of the sterically-hindered amine functional group, thus, making them superior biocidal materials for use in coatings exposed to sunlight and other sources of ultraviolet photons. Also, it will be possible to copolymerize the N-halaminesiloxane monomers taught herein with quaternary ammonium salt siloxane monomers to enhance solubility in aqueous solution and to provide a very long-term biocidal effect.

Also described herein are compositions comprising the compounds described above. One of skill in the art can determine additional compounds or compositions with which to combine the above compounds for a desired application. One of skill in the art can determine quantities of the compounds above to add to additional compounds or compositions for a desired application.

For example, the compounds above can serve as monomers for creating polymers and/or co-polymers. The compounds can also be combined with materials such as described below for producing biocidal materials.

The halogenated compounds described above can be used to inactivate pathogenic microorganisms, such as bacteria, fungi, and yeasts, as well as virus particles, which can cause infectious diseases, and those microorganisms which cause noxious odors and unpleasant coloring, such as mildew.

The N-halamine monomers and polymers taught herein represent a significant improvement over the siloxanes in US 2004/0127667 A1 in that they contain both amine and amide functional groups, which allow more biocidal halogen to be loaded per unit and increase stability over the N-halaminesiloxanes containing only available amide groups.

B. Synthetic Methods

Described herein is a method for making compounds having the formula I.

An unhalogenated precursor N-halaminesiloxane monomer can be synthesized, in a preferred method, by reacting 3-chloropropyltriethoxysilane or 3-chloropropyltrimethoxysilane with the potassium or sodium salt of 7,7,9,9-tetramethyl-1,3,8-triazaspiro[4.5]decane-2,4-dione in an aprotic solvent, such as dimethylformamide (DMF). The latter spiro compound can be synthesized by reaction of 2,2,6,6-tetramethyl-4-piperidone with ammonium carbonate and potassium cyanide in an ethanol/water solution, or it can be purchased from a vendor such as the Aldrich Chemical Company (Milwaukee, Wis.).

The chlorinated precursor monomers can be synthesized and rendered biocidal by reacting the corresponding unhalogenated precursor monomers suspended in water at ambient temperature with free chlorine from such sources as gaseous chlorine, sodium hypochlorite bleach, calcium hypochlorite, chloroisocyanurates, and dichlorohydantoins. In the case of the dichlorohydantoins, the chlorine moiety on the imide nitrogen should transfer to the more stable amide and amine nitrogens of the precursor monomers.

Likewise, the brominated precursor monomers can be prepared and rendered biocidal by exposing them in aqueous solution at ambient temperature to free bromine from such sources as molecular bromine liquid, sodium bromide in the presence of an oxidizer such as potassium peroxy monosulfate, and brominated hydantoins. Halogenation can also be effected in organic solvents employing free radical halogenating agents such as t-butyl hypochlorite.

The unhalogenated or halogenated precursor polymers can be prepared by exposure of the monomers to acid, e.g., HCl, at elevated temperature, e.g., about 100° C., then curing at temperatures as high as about 170° C., or the monomers can be reacted with a poly(3-chloropropyltriethoxysilane) or poly(3-chloropropyltrimethoxysilane) in DMF at about 100° C. Copolymerization with other siloxane monomers such as those containing quaternary ammonium functional groups so as to render the copolymers soluble in water could also be effected. Halogenation to form precursor halogenated polymers or copolymers is performed in the same manner as for the precursor monomers.

Alternative methods for making the compounds of the invention can be determined using techniques generally known to synthetic organic chemists.

C. Utility and Methods of Use

The compounds and/or compositions of the present invention can be used, for example, for producing a functionalized surface or material. An effective amount of a compound and/or composition of the present invention can be attached to or incorporated in a particular material. The method for attaching or incorporating the compound and/or composition is not critical as long as the activity of the compound/composition is maintained.

By the term "effective amount" of a compound or composition as provided herein is meant a sufficient amount of the compound or composition to provide the desired result, e.g., biocidal activity. The exact amount required may depend on the material to be functionalized. Thus, it is not possible to specify an exact "effective amount." However, an appropriate effective amount can be determined by one of ordinary skill in the art using only routine experimentation.

Examples of a material that can be functionalized are cellulose, chitin, chitosan, synthetic fibers, glass, ceramics, plastics, rubber, cement grout, latex caulk, porcelain, acrylic films, vinyl, polyurethanes, silicon tubing, marble, metals, metal oxides, silica, and mixtures thereof. The choice of material can be determined by one of ordinary skill in the art.

To give a material biocidal activity, the halogenated form of the compound/composition can be, for example, attached to or incorporated in the material. Alternatively, the non-halogenated compound/composition can be attached to or incorporated in the material and then subsequently halogenated.

Taught herein is a method of rendering a surface or material biocidal. The method can comprise adding a halogenated compound and/or composition of the invention to a material. Alternatively, a method can comprise adding an unhalogenated compound and/or composition of the invention to a material and subsequently halogenating the compound and/or composition. The unhalogenated compound or composition can be a monomer, polymer, or copolymer defined above, wherein X and X' are H. The unhalogenated composition/compound can be attached to a material through the hydroxyl moieties. The subsequent step of halogenation can be exposing the thus modified surface or material to a source of oxidative chlorine or bromine.

The halogenated or unhalogenated precursor monomers, polymers, or copolymers can be bound to a surface or material through either covalent bonding or an adhesive interaction, for example, depending on the nature of the surface or material. This can be accomplished by exposing the surface or material to a solution of the unhalogenated precursor monomer or polymer at temperatures in the range of about 0 to about 300° C., more preferably about 20 to about 150° C., depending upon the nature of the surface or material. This can also be accomplished by exposing the surface or material to a solution of the halogenated precursor monomer or polymer at temperatures in the range of 0 about to about 60° C., more preferably about 20 to about 40° C., depending upon the nature of the surface or material. The solvent for the precursor monomers and polymers can be organic materials such as ethanol or mixtures of these with water, although alcohols are less useful for the halogenated precursor copolymers because they partially protonate the nitrogen of the heterocyclic ring liberating halogen. If siloxane copolymers containing quaternary ammonium salt functional groups are used, the solvent can be water. Other additives can be introduced to the solutions of the monomers or polymers to enhance binding to the surface or materials, e.g., potassium thiocyanate for binding to cellulose. The solutions containing the monomers or polymers can be exposed to the surfaces or materials by soaking, spraying, spreading, and the like. Following drying of the solution on the surface, curing at some temperature (the value of which depends upon the surface or material composition, e.g., about 25° C. for paper, about 95° C. for cotton fibers and glass, etc.) for about 15 to about 120 minutes should be performed.

The surface or material can be rendered biocidal if the unhalogenated precursor monomer or polymer is employed by exposure to a source of oxidative halogen, such as an aqueous solution of sodium hypochlorite bleach, calcium hypochlorite, chloroisocyanurates, and dichlorohydantoins, or an organic solution of t-butyl hypochlorite, for chlorination, or an aqueous solution of molecular bromine liquid, sodium bromide in the presence of an oxidizer such as potassium peroxy monosulfate, and brominated hydantoins for bromination. For example, an aqueous solution of 5 to 10% Clorox® can be used for efficient chlorination which can be accomplished at ambient temperature by spraying or soaking the surface or material with same. After halogenation, the surface or material should be allowed to dry in air at temperatures up to about 40° C. (ambient temperature is preferable if time permits) and rinsed with water. The surface or material will then exhibit biocidal properties for various time periods dependent upon the composition of the surface or material, the use pattern (contact with organisms and halogen demand), the storage temperature, etc. When the bound halogen content becomes too low for efficient biocidal activity, the surface or material can be recharged with halogen in the same manner as for the original charging noted above.

An alternate method of attaching similar biocidal moieties to surfaces utilizing siloxane chemistry would be first to bond a siloxane functional group to the surface and then second to bond the heterocyclic N-halamine or precursor N-halamine group to the already tethered siloxane through a nucleophilic substitution reaction. For example, chloropropyltriethoxysilane can be used to bond the siloxane to the surface, and then the chloropropyl functionality, thus, tethered through the siloxane can be reacted with the alkali metal salt of 7,7,9,9-tetramethyl-1,3,8-triazaspiro[4.5]decane-2,4-dione to produce an anchored hydantoin precursor which can then be halogenated in situ as described above to render the surface biocidal.

One of skill in the art can determine alternative methods of attaching, incorporating or otherwise adding a compound/composition of the present invention to a material or surface.

The mechanism of action of the biocidal surfaces and materials produced from the precursor copolymers described herein is believed to be a result of surface contact of the organism with chlorine or bromine moieties covalently bound to the heterocyclic functional groups on the bound siloxane. The chlorine or bromine atoms are transferred to the cells of the microorganisms where they cause inactivation through a mechanism not completely understood, but probably involving oxidation of essential groups contained within the enzymes comprising the organisms.

A marked advantage of the biocidal surfaces and materials of this invention over prior technology is that they are much more effective biocidally against pathogenic microorganisms encountered in medical applications such as *Staphylococcus aureus* and *Pseudomonas aeruginosa* than are commercial biocides, such as the pure quaternary ammonium salts, so they can serve a dual function, i.e., inactivation of disease-causing pathogens and of odor-causing microorganisms. For this reason the invention will have wide-spread use in medical settings such as hospitals, nursing facilities, and research laboratories. It should also be useful for biocidal applications in a variety of other industrial settings as well as in the home. A few examples of surfaces and materials which can be made biocidal with this invention include envelopes, surgical gowns and gloves, sheets, bandages, sponges, table and counter tops, glassware, plastic items, synthetic fibers, wood, chitin, chitosan, cement grout, latex caulk, porcelain, acrylic films, vinyl, polyurethanes, silicon tubing, marble, and metals.

The present invention is more particularly described in the following examples which are intended as illustrative only since numerous modifications and variations therein will be apparent to those skilled in the art.

EXAMPLES

The following examples are put forth so as to provide those of ordinary skill in the art with a complete disclosure and description of how the compounds, compositions, articles, devices, and/or methods described and claimed herein are made and evaluated, and are intended to be purely exemplary and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

Example 1

Preparation of 7,7,9,9-tetramethyl-1,3,8-triazaspiro[4.5]decane-2,4-dione (TTDD)

In a Parr high-pressure reactor, 15.6 grams (0.1 mol) of 2,2,6,6-tetramethyl-4-piperidone (Aldrich Chemicals Inc.), 13.5 grams (0.2 mol) of 97% potassium cyanide, 43.2 grams (0.45 mol) of ammonium carbonate, 120 mL ethanol, and 120 mL water were mixed. The contents were reacted with stirring at 85° C. for 12 hours, cooled to ambient temperature, and poured into 300 mL of water causing the solid product to precipitate. Impurity salts were washed away with water, and the product was dried.

The product (white powder) was obtained in a 91% by weight yield. It had a decomposition point before melting at greater than 300° C.

The product could be chlorinated as a suspension in aqueous 12 vol % sodium hypochlorite at about pH 7 (achieved by addition of HCl) to produce about 80% of the loaded oxidative chlorine theoretically expected as determined by iodometric/thiosulfate titration.

Example 2

Preparation of Precursor N-Halaminesiloxane Monomer and Polymer

A precursor N-halaminesiloxane monomer as shown in structure I

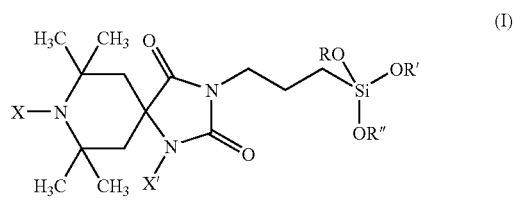

in which R, R', and R" are ethyl, and X and X' are H, was prepared by reaction of the potassium salt of the 7,7,9,9-tetramethyl-1,3,8-triazaspiro[4.5]decane-2,4-dione (TTDD) as described in Example 1 with 3-chloropropyltriethoxysilane.

The potassium salt was prepared by adding 10.2 grams (0.046 mol) of TTDD and 2.81 grams (0.05 mol) of potassium hydroxide to 100 mL of ethanol and refluxing for 10 minutes. Following removal of the ethanol solvent and water produced during salt formation, the dried solid salt was added to 100 mL of anhydrous DMF, and the solution was heated to 100° C. Then, 11.1 grams (0.046 mol) 3-chloropropyltriethoxysilane was added dropwise, and the mixture was heated with stirring at 100° C. for 8 hours. The potassium chloride produced was removed by filtration, and the DMF was removed by vacuum distillation to produce the product as a viscous oil in about 98% by weight yield.

The $^1$H NMR of the monomer was consistent with the structure illustrated above.

A polymer of the above precursor monomer was prepared in 92% by weight yield by an analogous procedure using the potassium salt of TTDD and poly(3-chloropropyltriethoxysilane) in anhydrous DMF. The poly(3-chloropropyltriethoxysilane) was prepared as described by Worley, et al. in U.S. published patent application US 2004/0127667 A1, hereby incorporated by reference for its teachings on preparation of poly(3-chloropropyltriethoxysilane).

Example 3

Preparing Wash-fast Biocidal Cotton

A bath containing a 5% by weight aqueous solution of the precursor unhalogenated N-halaminesiloxane monomer, synthesized as described in Example 2, was prepared. Swatches of Style 400 Bleached 100% cotton print cloth (Testfabrics, Inc.) were soaked in the bath for about 10 minutes and then cured at 95° C. for 2 hours.

Following the curing process, the swatches were soaked in a 0.5 wt % detergent (standard commercial consumer detergent) aqueous solution for 15 minutes, washed with water, and dried in air at 70° C. The swatches were then soaked in a 10 vol % solution of Clorox® in water at ambient temperature for 45 minutes, rinsed with water, and dried at 45° C. for 30 minutes.

An iodometric/thiosulfate titration indicated that the oxidative chlorine loading after this process was 0.495%. In other similar experiments (not described herein), chlorine loadings were varied from 0.41 to 0.88%.

The polymeric form of the unhalogenated N-halaminesiloxane described in Example 2 can be coated on cotton swatches with an analogous procedure and upon chlorination, provide chlorine loadings of about 0.30 to 0.91%.

Chlorinated swatches of the cotton coated with the precursor monomer of N-chloraminesiloxane described above and containing a 0.41% chlorine loading provided log reductions of *Staphylococcus aureus* (ATCC 6538) bacterial suspensions of 4.1, 4.6, and 6.4 (complete inactivation) at contact time intervals of 15, 30, and 60 minutes, respectively. Non-chlorinated swatches served as controls and showed no log reduction at the same contact times. All tests involved adding a 25 µL drop of inoculum to the test swatch, rinsing the swatch with distilled, deionized water after the contact time interval, and then plating to determine counts. For cotton containing higher chlorine loadings of 0.82% (monomer) or 0.90% (polymer), the reduction in *S. aureus* was 7.4 logs (complete kill) within 10 minutes contact and the same reduction for *Escherichia coli* in less than 15 minutes contact for the monomeric form, and complete 7.0 log reductions of both bacteria within 1 minute contact for the polymeric form. Thus, the chlorinated cotton swatches possessed adequate biocidal activity, and since the amine N—Cl functional group is very stable (more so than the amide N—Cl functional group), the coating materials are expected to have advantages over pure hydantoinyl siloxane coating materials which have only N—Cl amide functional groups in terms of longevity of biocidal action.

Example 4

Chlorine Stability on Biocidal Cotton

Cotton swatches coated with the monomeric and polymeric N-halaminesiloxanes as described in Example 3 were subjected to laundry washing cycles using MTCC Test Method 61 (Test 2A Procedure). The samples were evaluated after 5, 10, and 50 washing cycles for retention of the coating. Those samples not chlorinated before washing were chlorinated by the procedure described above in order to assess how much chlorine could be loaded after variable numbers of washing cycles. Some samples were chlorinated before washing and then rechlorinated after washing. In all cases, iodometric/thiosulfate titration was used to measure the chlorine loadings on the swatches. The results are shown in Table 1.

TABLE 1

Stability of the Monomeric N-halaminesiloxane Coatings on Cotton Subjected to Cycles of Washing Using AATCC Test Method 61.

| Number of Washing Cycles | % Cl$^+$ Loading after Washing and Chlorinated, Not Prechlorinated | % Cl$^+$ Loading after Washing, Prechlorinated | % Cl$^+$ Loading after Washing, Pre- and Rechlorinated |
| --- | --- | --- | --- |
| 0 | 0.80 | 0.80 | 0.80 |
| 5 | 0.40 | 0.57 | 0.66 |
| 10 | 0.30 | 0.49 | 0.60 |
| 50 | 0.04 | 0.29 | 0.42 |

The data in Table 1 indicate that the coating for the monomeric siloxane not prechlorinated gradually washed off over 50 washings, as only 0.04% chlorine could be loaded on to the cotton at this point. However, perchlorination reduced the loss rate of the coating, probably because the chlorinated hydantoinyl siloxane had increased hydrophobicity. Upon rechlorination of the latter, it was evident that only about half of the coating was lost during the 50 wash cycles. The data suggests that if some free chlorine (bleach) were added into each wash cycle, that the cotton would remain coated and biocidal for many more than 50 washes. The polymeric siloxane exhibited very similar behavior.

Example 5

Preparation of N-halamine/Quat Copolymers

Precursor N-halamine-quat-siloxane random copolymers can be prepared by simply controlling the ratio of TTDD and a tertiary amine in a reaction with poly(3-chloropropyltrialkoxysilane).

For example, in preparing a copolymer siloxane with about 50% N-halamine and 50% quat functional groups (% by number of groups), 6.92 grams (0.05 mol) of poly(3-chloropropyltriethoxysilane) were dissolved in 100 mL of DMF. Then, 6.57 grams (0.025 mol) of the potassium salt of 7,7,9,9-tetramethyl-1,3,8-triazaspiro[4.5]decane-2,4-dione and 5.62 grams (0.025 mol) of 95% dodecyldimethylamine were added, and the reaction mixture was stirred at 100° C. for 12 hours. After cooling to ambient temperature, the potassium chloride produced in the reaction was removed by filtration followed by removal of most of the DMF solvent by rotaevaporation. Hexane was then used to extract all of the remaining DMF. Drying overnight at 50° C. produced 11.99 grams of white solid product (about a 71% yield). The solubility in water of this product was about 3%.

Example 6

Enhancing the Solubility of the Precursor N-halaminesiloxane Polymer

The precursor siloxane polymer of TTDD is soluble in organic solvents, such as DMF and ethanol, but it is almost insoluble in water. However, there are possible applications in which water solubility may be desirable.

Water solubility can be effected by adding dilute acid to the polymer suspended in water. Protonation of the amine nitrogen of structure I occurs, greatly enhancing solubility.

For example, 1.0 gram of the polymer was completely dissolved in 19.0 grams of 0.1 N aqueous acetic acid solution. During a coating procedure, the amine nitrogen is deprotonated in the presence of basic detergent and/or bleach, such that it can then be N-chlorinated.

Example 7

Coating with 7,7,9,9-tetramethyl-1,3,8-triazaspiro [4.5]decane-2,4-dione Directly Surfaces such as cotton and polyester fibers can be coated with TTDD directly without a siloxane tether. In this manner, cotton fabric was soaked in a bath containing 2% by weight TTDD in water at pH 6 (using dilute acetic acid) at 60° C. for 30 minutes. The fabric was then dried at 50° C. for 60 minutes and then briefly soaked in 1 wt % aqueous sodium hydroxide (pH 12). Following drying at 150° C. for 5 minutes, the treated fabric was chlorinated in a 10 vol % aqueous solution of sodium hypochlorite bleach at pH 8 for 30 minutes. The fabric was then rinsed thoroughly with water and dried at 45° C. for 60 minutes to remove any occluded free chlorine.

A control cotton fabric which was not treated with TTDD was chlorinated in the same manner.

An iodometric/thiosulfate titration revealed a Cl$^+$ loading of 0.57% for the fabric treated with TTDD and 0% for the control. At this time, the fabric would be biocidal within a contact time of a few minutes. However, after 5 washing cycles (AATCC Test Method 61 (Test 2A Procedure)), the fabric sample contained no titratable chlorine and could not be rechlorinated. Similar results were obtained for basic-dyeable polyester.

The results obtained in this example show that indeed 7,7,9,9-tetramethyl-1,3,8-triazaspiro[4.5]decane-2,4-dione can be attached to surfaces such as fabrics and rendered biocidal by chlorination, but that the attachment is not as firm as through a siloxane tether, so the biocidal surfaces/fabrics without the tether would probably need to be of the disposable type, or at least be subject to minimal washing.

Throughout this application, various publications are referenced. The disclosures of these publications in their entireties are hereby incorporated by reference into this application in order to more fully describe the compounds, compositions and methods described herein.

Various modifications and variations can be made to the compounds, compositions and methods described herein. Other aspects of the compounds, compositions and methods described herein will be apparent from consideration of the specification and practice of the compounds, composition and methods disclosed herein. It is intended that the specification and examples be considered as exemplary.

What is claimed is:

1. A compound having the structure

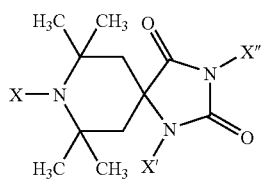

wherein X, X', and X" independently are H, Cl, or Br, wherein no more than two of X, X', and X" are H.

2. The compound of claim 1 wherein X, X', and X" are Cl.

3. The composition of claim 1 wherein X, X', and X" are Br.

4. A composition comprising the compound of claim 1.

5. A compound having the structure

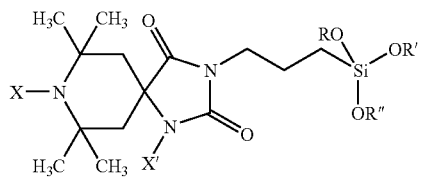

wherein R, R', and R" are independently alkyl groups containing 1 to 4 carbon atoms or hydrogen, and X and X' are independently H, Cl, or Br.

6. The compound of claim 5 wherein X and X' are each a hydrogen atom.

7. The compound of claim 5 wherein one of X or X' is Cl or Br and the other is H.

8. The compound of claim 5 wherein X or X' are independently Cl or Br.

9. The compound of claim 5 wherein R, R', and R" independently are methyl, ethyl, or hydrogen, and X and X' are each a hydrogen atom.

10. The compound of claim 5 wherein R, R', and R" independently are methyl, ethyl, or hydrogen, and wherein one of X or X' is Cl or Br and the other is H.

11. The compound of claim 5 wherein R, R', and R" independently are methyl, ethyl, or hydrogen, and wherein X and X' are each chlorine.

12. The compound of claim 5 wherein R, R', and R" independently are methyl, ethyl, or hydrogen, and wherein X and X' are each bromine.

13. A composition comprising the compound of claim 5.

14. A polymer comprising monomer units of a compound

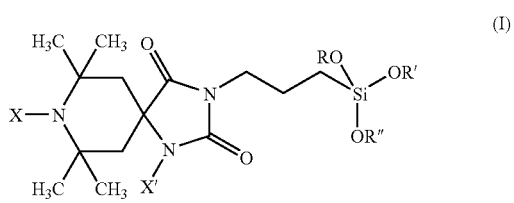

wherein R, R', and R" are independently alkyl groups containing 1 to 4 carbon atoms or hydrogen, and X and X' are independently H, Cl, or Br.

15. The polymer of claim 14 wherein R, R', and R" independently are methyl, ethyl, or hydrogen, and X and X' are each a hydrogen atom.

16. The polymer of claim 14 wherein R, R', and R" independently are alkyl groups containing 1 to 4 carbon atoms or hydrogen, and wherein one of X or X' is Cl or Br and the other is H.

17. The polymer of claim 16 wherein R, R', and R" independently are methyl, ethyl, or hydrogen.

18. The polymer of claim 14 wherein R, R', and R" independently are methyl, ethyl, or hydrogen, and wherein X and X' are each chlorine.

19. The polymer of claim 14 wherein R, R', and R" independently are methyl, ethyl, or hydrogen, and wherein X and X' are each bromine.

20. A copolymer comprising a monomer of the compound of claim 5.

21. A surface or material which is blended with or attached to a compound

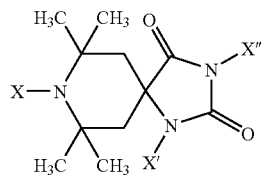

wherein X, X', and X" independently are H, Cl, or Br, wherein no more than two of X, X', and X" are H.

22. The surface or material of claim 21 which comprise cellulose, chitin, chitosan, synthetic fibers, glass, ceramics, plastics, rubber, cement grout, latex caulk, porcelain, acrylic films, vinyl, polyurethanes, silicon tubing, marble, metals, metal oxides, silica, or mixtures thereof.

23. A surface or material which is blended with or attached to a compound

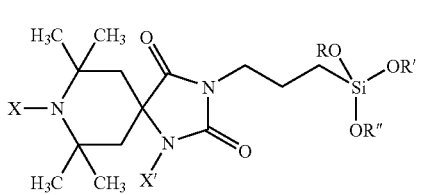

(I)

wherein R, R', and R" are independently alkyl groups containing 1 to 4 carbon atoms or hydrogen, and X and X' are independently H, Cl, or Br.

24. The surface or material of claim 23 which comprise cellulose, chitin, chitosan, synthetic fibers, glass, ceramics, plastics, rubber, cement grout, latex caulk, porcelain, acrylic films, vinyl, polyurethanes, silicon tubing, marble, metals, metal oxides, silica, or mixtures thereof.

25. A surface or material which is blended with or attached to a polymer comprising monomer units of

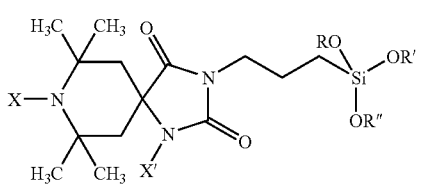

(I)

wherein R, R', and R" are independently alkyl groups containing 1 to 4 carbon atoms or hydrogen, and X and X' are independently H, Cl, or Br.

26. The surface or material of claim 25 which comprise cellulose, chitin, chitosan, synthetic fibers, glass, ceramics, plastics, rubber, cement grout, latex caulk, porcelain, acrylic films, vinyl, polyurethanes, silicon tubing, marble, metals, metal oxides, silica, or mixtures thereof.

27. A method of making a surface or material biocidal comprising providing compound

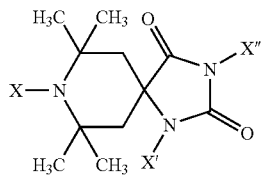

wherein X, X', and X" independently are H, Cl, or Br, wherein no more than two of X, X', and X" are H, and
attaching or adding the compound or a composition comprising the compound to a surface or material.

28. A method of making a surface or material biocidal comprising providing a compound

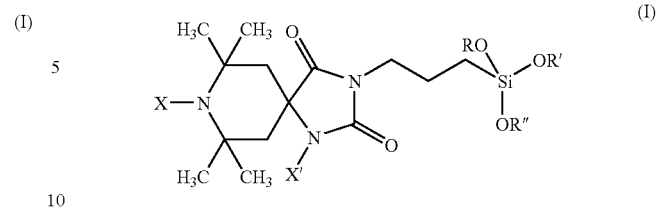

(I)

wherein R, R', and R" are independently alkyl groups containing 1 to 4 carbon atoms or hydrogen, and X and X' are independently H, Cl, or Br, wherein at least one of X and X' is a Cl or Br, and
attaching or adding the compound or a composition comprising the compound to a surface or material.

29. The method of claim 28 wherein the compound or composition is attached to the surface or material through the hydroxyl moieties.

30. A method of making a surface or material biocidal comprising providing a polymer comprising monomer units of a compound

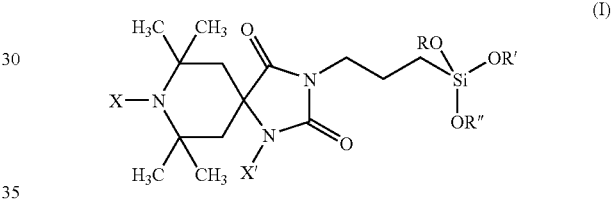

(I)

wherein R, R', and R" are independently alkyl groups containing 1 to 4 carbon atoms or hydrogen, and X and X' are independently H, Cl, or Br and wherein at least one of X and X' is a Cl or Br, and
attaching or adding the polymer or a composition comprising the polymer to a surface or material.

31. The method of claim 30 wherein the polymer is attached to the surface or material through the hydroxyl moieties.

32. A method of making a surface or material biocidal comprising providing a compound

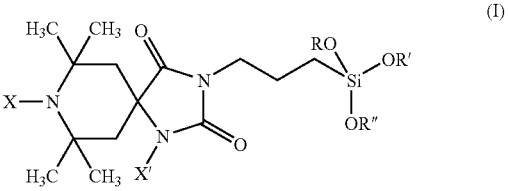

(I)

wherein R, R', and R" are independently alkyl groups containing 1 to 4 carbon atoms or hydrogen, and X and X' are independently H, Cl, or Br.
attaching or adding the compound or a composition comprising the compound to a surface or material, and
exposing the surface or material with the compound or composition to a source of oxidative chlorine or bromine.

33. The method of claim 32 wherein the compound or composition is attached through the hydroxyl moieties.

34. A method of making a surface or material biocidal comprising providing a polymer comprising monomer units of a compound

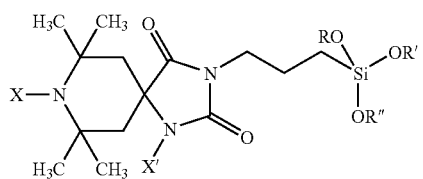
(I)

wherein R, R', and R" are independently alkyl groups containing 1 to 4 carbon atoms or hydrogen, and X and X' are independently H, Cl, or Br, attaching or adding the polymer or a composition comprising the polymer to a surface or material, and exposing the surface or material with the polymer or composition to a source of oxidative chlorine or bromine.

* * * * *

UNITED STATES PATENT AND TRADEMARK OFFICE
CERTIFICATE OF CORRECTION

PATENT NO. : 7,335,373 B2
APPLICATION NO. : 10/991358
DATED : February 26, 2008
INVENTOR(S) : Shelby D. Worley et al.

It is certified that error appears in the above-identified patent and that said Letters Patent is hereby corrected as shown below:

At column 5, line 27, please remove the space between "7,7,9,9-tetra" and "methyl-1,3,8-triazaspiro[4.5]decane-2,4-dione"

At column 13, line 30, please replace "MTCC" with -- AATCC --

Signed and Sealed this

Seventeenth Day of June, 2008

JON W. DUDAS
*Director of the United States Patent and Trademark Office*